United States Patent
Tomulewicz

(10) Patent No.: US 10,213,469 B2
(45) Date of Patent: Feb. 26, 2019

(54) HERBAL PREPARATION FOR ACCELERATING WOUNDS AND SKIN INFLAMMATIONS HEALING AND ITS APPLICATION

(71) Applicant: WYŻSZA SZKOŁA MEDYCZNA W BIAŁYMSTOKU, Białystok (PL)

(72) Inventor: Mikolaj Tomulewicz, Bialystok (PL)

(73) Assignee: Wyzsza Szkola Medyczna w Bialymstoku, Bialystok (PL)

( * ) Notice: Subject to any disclaimer, the term of this patent is extended or adjusted under 35 U.S.C. 154(b) by 0 days.

(21) Appl. No.: 16/035,601

(22) Filed: Jul. 14, 2018

(65) Prior Publication Data

US 2018/0318375 A1    Nov. 8, 2018

Related U.S. Application Data

(63) Continuation-in-part of application No. 15/201,619, filed on Jul. 5, 2016.

(30) Foreign Application Priority Data

Jul. 9, 2015    (PL) .................................. P.413074
Oct. 2, 2015    (EP) .............................. EP15460092

(51) Int. Cl.

| A61K 36/00 | (2006.01) |
| A61K 36/53 | (2006.01) |
| A61K 9/06 | (2006.01) |
| A61K 9/00 | (2006.01) |
| A61K 47/18 | (2017.01) |
| A61K 47/38 | (2006.01) |
| A61P 17/02 | (2006.01) |
| A61K 47/10 | (2017.01) |

(52) U.S. Cl.
CPC ............ *A61K 36/53* (2013.01); *A61K 9/0014* (2013.01); *A61K 9/06* (2013.01); *A61K 47/10* (2013.01); *A61K 47/18* (2013.01); *A61K 47/38* (2013.01); *A61P 17/02* (2018.01); *A61K 2236/33* (2013.01)

(58) Field of Classification Search
CPC ..................................................... A61K 36/00
See application file for complete search history.

(56) References Cited

FOREIGN PATENT DOCUMENTS

RU    2450836 C1 *  5/2012

OTHER PUBLICATIONS

Grujic et al, Evaluation of antioxidant activity of *Melittis melissophyllum* L. extracts. Archives of Biological Sciences (2014), vol. 66, No. 4, pp. 1401-1410. (Year: 2014).*

* cited by examiner

*Primary Examiner* — Qiuwen Mi
(74) *Attorney, Agent, or Firm* — Andrew Malarz, Esq.

(57) ABSTRACT

The invention relates to a herbal preparation which can be applied in a wound and skin inflammation healing. The herbal preparation is characterized in that the preparation contents of emulsified or suspended in an organic medium extract of *Melittis melissophyllum* L. from 10% to 40% w/w and ethyl alcohol from 10% to 20% w/w. In case of an ointment as an organic medium was used vaseline album from 40% to 70% w/w, in case of a gel—glycerol or propylene glycol 2% w/w, triethylamine 2% w/w, hydroxycellulose 1% w/w and purified water, aqua purificata, from 30% to 35% w/w.

10 Claims, No Drawings ably treated the surface skin inflammations can cause an infection. A healing process is painful and often limits mobility and decreases quality of life of a patient.

HERBAL PREPARATION FOR ACCELERATING WOUNDS AND SKIN INFLAMMATIONS HEALING AND ITS APPLICATION

CROSS-REFERENCE TO RELATED APPLICATIONS

This a non-provisional application, being filed under section 35 U.S.C. 111(a), is a continuation-in-part application of the earlier application Ser. No. 15/201,619, filed Jul. 5, 2016, that claims benefits of the Polish Patent Application No. P.413074, filed on Jul. 9, 2015, and of the European Patent Application No. EP15460092, filed on Oct. 2, 2015, pursuant to section 35 U.S.C. 119, and provisions of the Paris Convention Treaty, contents of which are incorporated herein by reference.

BACKGROUND OF THE INVENTION (1) Field of the Invention

A subject matter of the present invention is a herbal preparation with anti-inflammatory and astringent effects used in a herbal medicine to treat conditions-related to interruption of anatomical continuity of outer layers of skin or deeper tissues.

(2) Description of Related Art Including Information Disclosed Under 37 CFR 1.97 and 37 CFR 1.98

Herbal preparations are widely used in herbal medicine, cosmetology, and conventional medicine. They have special properties due to presence of biologically active substances that act on skin after their application.

Surface skin inflammations constitute a very serious skin care problem. When untreated or inadequately treated the surface skin inflammations can cause an infection. A healing process is painful and often limits mobility and decreases quality of life of a patient.

A serious and still current problem in medicine is a rate of healing of various wounds inflicted by mechanical factors like abrasions, cuts, and wound cuts, as well as wounds caused by thermal or chemical factors like burns, or by other diseases complication such as diabetes and an associated with it problem of diabetic foot.

All significant injuries lead to damage of vessels and interruption of their anatomical continuity thereby initiating a molecular and cellular response leading to hemostasis, a process that causes bleeding to stop by keeping blood within a damaged blood vessel. This is the first stage of a wound healing.

The healing process cannot be initiated until hemostasis mechanisms start to work, what is a multifactorial and a multistep process. The most important element of hemostasis is blood clotting, leading to clot formation. A blood clot consists mainly of a mesh of fibrin and embedded on it platelets. The clot formation is a very important process. It prevents further loss of fluids and electrolytes from a wound and reduces pollutions coming from outside environment.

The healing process of skin can be accelerated by actions of all kind of chemical substances mainly of synthetic origin which often give rise to additional side effects mainly weakening elasticity of the skin what destructively affects contained in it proteins.

A current treatment of the above-referenced disorders generally involves use of an ointment with steroids and in cases of disorders with chronic conditions, with presence of a variety of bacteria, use of strong antibiotics which often cause adverse side effects.

Another way of treating skin injuries is use of calendula ointment, which contains calendula and Vaseline. When such ointment is used, however, the healing process is slower, and microorganisms can easily be reproduced on a crust formed on wound surface.

In a treatment of a skin inflammation, including wounds, also special herbal compositions with a synergistic effect are used.

From the publication No. WO 9742963A2 of the Patent Application, titled "Green Ointment", an ointment for a treatment of wounds and burns is known. It comprises in its composition plantains, chamomile, calendula, yarrow, gumtree, matricary, olive oil, eucalyptus, and celandine. An application of the ointment enables widening of assortment of medicinal preparations for burns and wounds and provides treatment efficiency of about 42%.

From the U.S. Pat. No. 5,061,491, titled "Medicinal Agent and Method for Treatment of Mastitis in Animals and Humans", a medicinal agent is known consisting of a mixture of a decoction of mixture of medicinal herbs in equal parts by weight and an ammonia solution infusion of the same medicinal herbs namely: wild chamomile, port marigold, stringing nettle, common centaury, pine buds, common plantain, birch buds, pot marjoram, garden sage, garden angelica, dandelion, coltsfoot, great burnet, common valerian, peppermint, common thyme, and tripartite burmarigold. The medicinal agent taught by that reference is highly effective and its application results in 98 to 100-percent recovery in a treatment of mastitis.

From the Polish Patent No. P.198268, titled "Herbal Composition for Treatment of Chronic Wounds", a herbal composition is known used particularly in a treatment of venous ulcers and postphlebitic syndrome, which contains a mixture of herbs consisting of marigold flower, herb firefly plantain, chamomile, and echinacea, wherein the herbal composition comprises active ingredients in the form of carotenoids, iridoids, aucubin, catalpol and polyphenols, particularly flavonoid and phenolic acids in the amount resulting from the ratio contained in composition of plants.

There is a trend in world medicine of seeking natural substances that may replace synthetic ones in a treatment of skin injuries.

SUMMARY OF THE INVENTION

Purposes of the Invention

It is an object of the present invention to widen an application of medical preparations, based on a herbal extract for a treatment of conditions associated with interruption of anatomical continuity of outer layers of skin or deeper tissues, which leads to an accelerated healing process and obtaining desired results even in the treatment of chronic and inflammatory complications after a surgery. This and other objects and advantages of the present invention will become apparent from a detailed description which follows.

BRIEF DESCRIPTION OF THE INVENTION

It was established, based on experiments, that the herbal preparation according to the present invention has comparable bactericidal and bacteriostatic properties with pharmacological formulations. The herbal preparation has an exacerbated therapeutic effect leading to rapid self-cleaning of a skin inflammation with interruption of the anatomical continuity of the outer layers or the deeper tissues and leading to their complete healing without causing side effects.

The herbal preparation, according to the present invention, contains a plant extract emulsified or suspended in an organic based medium, characterized in that it contains, as an active substance, an alcoholic extract from *Melittis melissophyllum* L., and other active substances such as flavonoids in the amount of from 3.6% to 13.4% by weight, polyphenols in the amount of from 11.25% to 45% by weight, tannins in the amount of from 5% to 8% by weight, amine compounds in the amount of from 0.475% to 1.9% by weight, bitter substances in the amount of from 11.55% to 46.2% by weight, and mineral salts in the amount of from 6% to 10% by weight.

The alcoholic extract of melittis contains a *Melittis melissophyllum* L. herb in the amount from 10% to 40% w/w, and ethyl alcohol in the amount from 10% to 20% w/w.

The herbal preparation in the form of an ointment contains, as an organic basis, Vaseline album in the amount from 40% to 70% w/w.

According to an aspect of one preferred embodiment of the invention, the herbal preparation, in the form of an ointment or gel, contains as an organic basis glycerol or propylene glycol in the amount of 2% w/w, trimethylamine in the amount of 2% w/w, hydroxycellulose in the amount of 1% w/w, and purified water (aqua purificata) in the amount from 30% to 35% w/w.

Another aspect of the present invention is use of the herbal preparation to treat various types of wounds and skin inflammations.

The herbal preparation, according to the present invention, causes normal growth of epithelium and accelerates granulation of skin tissues. It helps to maintain, for a longer period of time, moisture of wound environment what accelerates a wound filling, where due to a long lapse of time destruction of connective and subcutaneous tissue occurred, and accelerates a growth of epidermis.

The herbal preparation, based on the herbal extract from melittis (*Melittis melissophyllum* L.), contains various active substances such as tannins, polyphenols, flavonoids, amine compounds, bitter substances and mineral salts. All components of the herbal extract, with their percentage content in the entire extract, are listed in a table below. The percentage content of each component was determined by application of gas chromatography method with mass spectrometry (GC-MS).

| Compound | RI$^{eks.}$ | RI$^{lit.}$ | Content (%) |
| --- | --- | --- | --- |
| Ethylene glycol, di-TMS | 992 | 994 | 0.04 |
| Lactic acid, di-TMS | 1071 | 1073 | 0.09 |
| Glycolic acid, di-TMS | 1086 | 1083 | 0.04 |
| 3-Hydroxypropionic acid, di-TMS | 1154 | — | 0.05 |
| Glycerol, tri-TMS | 1294 | 1292 | 4.42 |
| Benzeneacetic acid, TMS | 1299 | 1299 | 0.03 |
| Succinic acid, di-TMS | 1324 | 1324 | 0.54 |
| Glyceric acid, tri-TMS | 1351 | 1348 | 0.07 |
| 3,4-Dihydrocoumarin | 1377 | 1378 | 0.07 |
| Hydroquinone, di-TMS | 1408 | 1410 | 0.05 |
| Coumarin | 1431 | 1432 | 3.01 |
| Malic acid, tri-TMS | 1511 | 1512 | 0.19 |
| Cinnamic acid, TMS | 1544 | 1549 | 0.04 |
| Tyrosol, di-TMS | 1578 | 1582 | 0.10 |
| 2-Hydroxyphenylpropanoic acid, di-TMS | 1690 | — | 3.15 |
| Vanillic acid, di-TMS | 1775 | 1776 | 0.03 |
| Azelaic acid, di-TMS | 1808 | 1808 | 0.10 |
| o-Coumaric acid, di-TMS | 1815 | 1811 | 1.54 |
| Protocatechuic acid, tri-TMS | 1836 | 1837 | 0.05 |

-continued

| Compound | RI$^{eks.}$ | RI$^{lit.}$ | Content (%) |
| --- | --- | --- | --- |
| Quinic acid, penta-TMS | 1901 | 1901 | 2.48 |
| Phytol, TMS | 2183 | 2187 | 1.02 |
| Campesterol, TMS | 3253 | 3251 | 0.13 |
| Stigmasterol, TMS | 3284 | 3285 | 0.33 |
| β-Sitosterol, TMS | 3341 | 3345 | 0.78 |
| Carbohydrates, among others: | | | 57.19 |
| α-Fructofuranose, penta-TMS | 1846 | 1843 | 2.80 |
| β-Fructofuranose, penta-TMS | 1855 | 1854 | 8.93 |
| α-Glucopyranose, penta-TMS | 1933 | 1932 | 7.64 |
| β-Glucopyranose, penta-TMS | 2032 | 2032 | 7.44 |
| Saccharose, octa-TMS | 2715 | 2714 | 8.81 |
| Fatty acids, among others: | | | 18.03 |
| Palmitic acid, TMS | 2052 | 2052 | 5.13 |
| Linoleic acid, TMS | 2214 | 2215 | 1.69 |
| Linolenic acid, TMS | 2223 | 2218 | 9.95 |
| Amino acids | | | 0.19 |
| Resin acids | | | 1.47 |
| Other compounds | | | 4.77 |

RI$^{eks.}$ Extract retention index, and for comparison with the database
RI$^{lit.}$ Extract retention index from literature.
Content (%) total record of the % share of compounds (calculated from the chromatogram for individual files)

The studies which led to the present invention showed the highest amounts of tannins in the herbal preparation having astringent properties and ability to create, especially with collagen, insoluble and irreversible connections which are not subject to putrefaction.

Moreover, tannins act astringently on mucous membranes, inhibit their permeability, preventing microbleeds from blood capillaries. The tannins also inactivate bacteria and their toxins, and have anti-inflammatory properties.

In addition, according to the present invention, flavonoids as a means of sealing walls of small blood vessels have been used as an anti-bleeding substance, preventing ecchymosis and varicose veins. Their activity is associated with inhibition of enzymes present in vessel walls—hyaluronidase, which is responsible for degradation of one of the intracellular substances and increase permeability of spaces between cells. It have also been established that flavonoids have an anti-aggregation effect on platelets.

Inclusion of *Melittis melissophyllum* L. to cultivation resulted in obtaining, on the one hand, a standardized raw material with specified quality parameters, and on the other hand, an increase of population of this plant in its natural environment, thus reducing risk of its extinction.

DETAILED DESCRIPTION OF INVENTION AND PREFERRED EMBODIMENTS

The present invention is explained in details in examples below. The examples should not, however, be perceived as limitation of the essence of the invention or to reduce the scope of the invention to be protected, since they are only provided as an illustration.

According to the invention the herbal preparation, containing an extract from *Melittis melissophyllum* L., is used to treat wounds of an epidermis and deeper layers of skin where inflammatory processes have occurred.

EXAMPLE I

A following semi-solid preparation was prepared for the study which was obtained by mixing together:
  40% w/w *Melittis melissophyllum* L. from the whole plant,
  20% w/w of 96% ethyl alcohol, 40% w/w Vaseline album—a hydrocarbon based substance used in lipophilic ointments.

The substance, etched by ethyl alcohol, is dissolved with help of heat in a smooth ointment medium for better dispersion of biologically active substances contained in the test extract. It could also be mixed in a cold lipophilic medium. It is important that the substance has been dissolved in the medium at the concentration below saturation.

In the study three groups of mammals with open wounds were involved:

I control group—no treatment was applied to the wound, even antiseptic one.

II group—a typical antiseptic agent was used, chlorhexidine, in accordance with a standard protocol regarding a treatment of an infected wound.

III group—the herbal preparation with a *Melittis melissophyllum* L. extract was used.

Phagocytic activity of white blood cells was assessed using phagocytic index (PI)—a percentage of phagocytes containing absorbed latex particles, and an amount of phagocytes (IF)—the average number of particles per phagocyte.

Tests results of an impact of application of the alcoholic extract of *Melittis melissophyllum* L. during epithelialization (epidermal) and the wound healing in mammals are showed in Table 1.

Test results determining a level of phagocytic activity of leukocytes in healing of the wound surface after application of the alcoholic extract of *Melittis melissophyllum* L. in mammals are showed in Table 2.

TABLE 1

| | Group | | |
|---|---|---|---|
| | Control | Chlorhexidine | *Melittis melissofillum* L. |
| Beginning epitelialization, 24-hours | 5.0 ± 0.4 | 3.9 ± 0.4 | 3.5 ± 0.2 |
| Beginning of rejection of the crust, 24-hours | 9.0 ± 0.5 | 7.6 ± 0.5 | 6.5 ± 0.4 |
| Full crust rejection, 24-hours | 11.5 ± 0.3 | 10.5 ± 0.3 | 7.8 ± 0.5 |
| Complete wound healing, 24-hours | 13.00 ± 0.91 | 11.25 ± 0.19 | 9.3 ± 0.7 |

TABLE 2

| | Time after granulation | | | | | |
|---|---|---|---|---|---|---|
| | 3 day | | 5 day | | 7 day | |
| Group | PI, % | IF | PI, % | IF | PI, % | IF |
| Control | 54.60 ± 1.12 | 7.0 ± 1.2 | 82.00 ± 2.28 | 11.0 ± 2.5 | 66.20 ± 4.16 | 12.5 ± 3.0 |
| Chlorhexidine | 61.60 ± 9.49 | 10.0 ± 2.5 | 59.01 ± 4.58 | 14.0 ± 3.0 | 48.20 ± 5.51 | 11.0 ± 3.0 |
| *Melittis melissofillum* L. | 82.40 ± 1.40 | 16.0 ± 3.5 | 89.00 ± 0.45 | 22.0 ± 2.8 | 41.20 ± 3.50$^a$ | 9.0 ± 1.5 |

PI = FI—phagocytic index—the percentage of phagocytes containing latex particles.
IF = FF—the amount of phagocytes—the average number of particles per 1 phagocyte.

It was established during the tests that the extract from *Melittis melissophyllum* L. accelerates the wounds healing in the experimental group of mammals as compared to the wounds healing in the control group. The first regional crust rejection in the third group started in 6-7 days. In the control groups, in saline or chlorhexidine, in 9 and 7-8 days, respectively. The final crust rejection in the third group took place in 7-8 days. In the control group in 10-11 days. Animals receiving the herbal extract from *Melittis melissophyllum* L. had complete epithelialization of the wound surface on the 9-th day, while in the control group, having saline solution or chlorhexidine applied to the wound surface, a full epithelialization of the wound surface was observed on the 12-th or 13-th day.

The established phagocytic activity of neutrophil white blood cells from the wound surface in different periods of the wound healing, i.e. an increase in phagocytic index and number of phagocytes due to presence of the *Melittis melissophyllum* L. extract, is shown in Table 2. It was found for the first time that the *Melittis melissophyllum* L. extract has a high therapeutic activity during a wound healing period in all stages of the wound healing, accelerating the wound repair process and cells proliferation, therefore ensuring the complete wound healing much earlier.

Mechanisms of action of the *Melittis melissophyllum* L. extract are apparently caused by vasodilation and normalization of microcirculation disorders, improved metabolism of tissues, increased amount and phagocytic activity of neutrophils from the surface of the healing wounds and skin, and macrophage activation, directly or indirectly affecting proliferation of fibroblasts and angiogenesis.

Example II

A following herbal preparation was prepared for the study consisted of:
  40% w/w of the alcoholic extract of *Melittis melissophyllum* L. obtained from the whole plant and etching of dry raw a material by 96% ethyl alcohol,
  20% w/w of 96% ethyl alcohol,
  glycerol in the amount of 2%w/w,
  triethyloamnie in the amount of 2% w/w,
  hydroxycellulose in the amount of 1% w/w,
  purified water (aqua purificata) in the amount of 35% w/w.

The herbal preparation applied in a treatment of open wounds. It was used in a similar way as described in Example I. The experiment confirmed that the herbal preparation based on *Melittis melissophyllum* L. definitely accelerates repair processes during the wound healing. The complete wound healing was accomplished significantly faster than when applying typical antiseptic agents.

The invention claimed is:

1. A herbal preparation in the form of an ointment comprising a plant extract emulsified or suspended in an organic based medium characterized in that it contains, as an active substance, an alcoholic extract from *Melittis melissophyllum* L., and other active substances namely flavonoids in the amount of from 3.6% to 13.4% by weight, polyphenols in the amount of from 11.25% to 45% by weight, tannins in the amount of from 5% to 8% by weight, amine compounds in the amount of from 0.475% to 1.9% by weight, bitter substances in the amount of from 11.55% to 46.2% by weight, and mineral salts in the amount of from 6% to 10% by weight, used for an accelerated treatment of wounds and skin inflammations accompanied by an increase in the amount and phagocytic activity of neutrophils from the surface of the healing wounds and skin, without causing side effects.

2. The herbal preparation according to claim 1 characterized in that the alcoholic extract of melittis contains a

*Melittis melissophyllum* L. herb in the amount from 10% to 40% w/w, and ethyl alcohol in the amount from 10% to 20% w/w.

3. The herbal preparation according to claim 2 characterized in that it contains as an organic basis petroleum jelly in the amount from 40% to 70% w/w.

4. The herbal preparation according to claim 2 characterized in that it contains as an organic basis comprising glycerol or propylene glycol in the amount of 2% w/w, trimethylamine in the amount of 2% w/w, hydroxycellulose in the amount of 1% w/w, and purified water, aqua purificata, in the amount from 30 to 35% w/w.

5. The herbal preparation according to claim 1 characterized in that it is used for an accelerated treatment of chronic and inflammatory complications after a surgery without causing side effects.

6. The herbal preparation according to claim 1 characterized in that it leads to a normal growth of epithelium and epidermis, accelerates granulation of skin tissues, maintains moisture of wound environment, and to self-cleaning of the skin inflammations.

7. The herbal preparation according to claim 1 characterized in that it comprises the highest amounts of tannins with astringent properties and ability to create, with collagen, insoluble and irreversible connections that are not subject to putrefaction.

8. The herbal preparation according to claim 7 characterized in that the tannins act astringently on mucous membranes, inhibit their permeability, prevent microbleeds from blood capillaries, inactivate bacteria and their toxins, and have anti-inflammatory properties.

9. A herbal preparation in the form of an ointment comprising a mixture of 40% w/w of an alcoholic extract from *Melittis melissophyllum* L. obtained from extracting a whole dry raw plant material by 96% ethyl alcohol, 20% w/w of 96% ethyl alcohol, glycerol in the amount of 2% w/w, triethylamine in the amount of 2% w/w, hydroxycellulose in the amount of 1% w/w, and purified water, aqua purificata, in the amount of 35% w/w, used for an accelerated treatment of wounds and skin inflammations without causing side effects.

10. The herbal preparation according to claim 9 wherein presence of *Melittis melissophyllum* L. accelerates repair processes of tissues during a treatment of the wounds and skin inflammations.

* * * * *